(12) United States Patent
Hossainy et al.

(10) Patent No.: US 8,734,817 B2
(45) Date of Patent: *May 27, 2014

(54) HYALURONIC ACID BASED COPOLYMERS

(71) Applicant: Advanced Cardiovascular Systems, Inc., Santa Clara, CA (US)

(72) Inventors: Syed Faiyaz Ahmed Hossainy, Hayward, CA (US); Eugene Michal, San Francisco, CA (US); Thierry Glauser, Redwood City, CA (US); Connie Kwok, Washington, WA (US); Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/631,399

(22) Filed: Sep. 28, 2012

(65) Prior Publication Data
US 2013/0023509 A1    Jan. 24, 2013

Related U.S. Application Data

(62) Division of application No. 10/835,912, filed on Apr. 30, 2004, now Pat. No. 8,293,890.

(51) Int. Cl.
*A61K 9/00* (2006.01)
*C08F 251/00* (2006.01)

(52) U.S. Cl.
USPC .......................................... 424/400; 527/300

(58) Field of Classification Search
None
See application file for complete search history.

(56) References Cited

U.S. PATENT DOCUMENTS

| | | | |
|---|---|---|---|
| 3,839,309 A | 10/1974 | Keyes et al. | |
| 4,806,621 A | 2/1989 | Kohn et al. | |
| 4,956,489 A | 9/1990 | Auriol et al. | |
| 5,026,821 A | 6/1991 | Boustta et al. | |
| 5,443,907 A | 8/1995 | Slaikeu et al. | |
| 5,464,650 A | 11/1995 | Berg et al. | |
| 5,470,911 A | 11/1995 | Rhee et al. | |
| 5,476,909 A * | 12/1995 | Kim et al. | 525/408 |
| 5,624,411 A | 4/1997 | Tuch | |
| 5,849,368 A | 12/1998 | Hostettler et al. | |
| 6,103,255 A | 8/2000 | Levene et al. | |
| 6,153,252 A | 11/2000 | Hossainy et al. | |
| 6,288,043 B1 * | 9/2001 | Spiro et al. | 514/54 |
| 6,503,538 B1 | 1/2003 | Chu et al. | |
| 6,503,556 B2 | 1/2003 | Harish et al. | |
| 6,525,145 B2 * | 2/2003 | Gevaert et al. | 525/450 |
| 6,534,560 B2 | 3/2003 | Loomis et al. | |
| 6,630,457 B1 * | 10/2003 | Aeschlimann et al. | 514/54 |
| 6,946,499 B2 | 9/2005 | Loomis et al. | |
| 7,091,191 B2 | 8/2006 | Laredo et al. | |
| 7,202,064 B2 | 4/2007 | Skraly et al. | |
| 7,368,169 B2 | 5/2008 | Kohn et al. | |
| 7,511,083 B2 | 3/2009 | Madsen et al. | |
| 2002/0032477 A1 | 3/2002 | Helmus et al. | |
| 2002/0087123 A1 | 7/2002 | Hossainy et al. | |
| 2002/0161376 A1 | 10/2002 | Barry et al. | |
| 2002/0183858 A1 | 12/2002 | Contiliano et al. | |
| 2003/0012765 A1 | 1/2003 | Thompson et al. | |
| 2003/0050422 A1 | 3/2003 | Bezemer et al. | |
| 2003/0059463 A1 | 3/2003 | Lahtinen | |
| 2003/0083732 A1 | 5/2003 | Stinson | |
| 2003/0100830 A1 | 5/2003 | Zhong et al. | |
| 2003/0100937 A1 | 5/2003 | Tsuboi et al. | |
| 2003/0104028 A1 | 6/2003 | Hossainy et al. | |
| 2003/0125800 A1 | 7/2003 | Shulze et al. | |
| 2003/0143315 A1 | 7/2003 | Pui et al. | |
| 2003/0161938 A1 | 8/2003 | Johnson | |
| 2004/0106987 A1 | 6/2004 | Palasis et al. | |
| 2005/0089970 A1 | 4/2005 | Bradburne et al. | |
| 2005/0129731 A1 | 6/2005 | Horres et al. | |
| 2005/0152949 A1 | 7/2005 | Hotchkiss et al. | |

FOREIGN PATENT DOCUMENTS

| | | |
|---|---|---|
| EP | 1 270 018 | 1/2003 |
| JP | 8-333402 | 12/1996 |
| WO | WO 0041739 | 7/2000 |
| WO | WO 02/06373 | 1/2002 |
| WO | WO 0206373 A1 * | 1/2002 |

OTHER PUBLICATIONS

Moriyama et al. Journal of Controlled Release 1999 59:77-86.*
Kim et al. Biomaterials 2003 24:4671-4679.*
Bulpitt et at., Journal of Biomedical Materials Research 1999, 47:152-169.
Kirkeretat. Biomaterials 2002 23:36613671.
Liu et at., Advances in Polymer Technology 1992, 11 : 249-262.
Sousa et al., New frontiers in cardiology Drug-eluting stents: part I. Circulation 2003, 107: 2274-2279.
Bullesfeld et al., "Long term evaluation of paclitaxel-coated stents for treatment of native coronary lesions", Z. Kardiol. 92, pp. 825-832 (2003).

(Continued)

*Primary Examiner* — Juliet Switzer
*Assistant Examiner* — Caralynne Helm
(74) *Attorney, Agent, or Firm* — Squire Sanders (US) LLP

(57) ABSTRACT

Hyaluronic acid (HA) conjugates or crosslinked HAs compositions for coating an implantable device are provided. The implantable device can be used for treating a disorder such as atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

10 Claims, 1 Drawing Sheet

(56) References Cited

OTHER PUBLICATIONS

Grube at al., "Safety and Performance of a Pacilitaxel-Eluting Stent for the Treatment of in-Stent Restenosis: Preliminary Results of the Taxus III Trial", J. of Am. Coll. Of Cardiology 39, Abstract 1 pg. (2002).

Grube et al., "Six-and Twelve-Month Results from a Randomized, Double-Blind Trial on a Slow-Release Paclitaxel-Eluting Stent for De Novo Coronary Lesions", Circulation 107, pp. 38-42 (2003).

Hwang et al., "Physiological Transport Forces Govern Drug Distribution for Stent-Based Delivery", Circulation 104, pp. 600-605 (2001).

Lambert et al., "Localized Arterial Wall Drug Delivery From a Polymer-Coated Removable Metallic Stent", Circulation vol. 90, issue 2, pp. 1003-11(1994).

Lincoff et al., "Sustained Local Delivery of Dexamethasone by a Novel Intravascular Eluting Stent to Prevent Restenosis in the Porcine Coronary Injury Model", JACC vol. 29, No. 4, pp. 808-16 (1997).

Luo et al., "Cross-linked hyaluronic acid hydrogel films: new biomaterials for drug delivery", J. of Controlled Release 69, pp. 169-184 (2000).

Tanabe et al., "In-Stent Restenosis Treated With Stent-Based Delivery of Paclitaxel Incorporated in a Slow-Release Polymer Formulation", Circulation 107, pp. 559-564 (2003).

Van Der Giesen et al. "Marked Inflammatory Sequelae to Implantation of Biodegradable and Nonbiodegradable Polymers in Porcine Coronary Arteries", Circulation vol. 94, issue 7, pp. 1690-7 (1996).

Clark "Reduction of Carboxylic Acids", www.chemguide.co.uk/organicprops/acids/reduction.html, 3 pgs. (2004).

Grinstaff at al., "Photocrosslinkable polymers for biomedical applications", Polymer Preprints 42(2), pp. 101-102 (2001).

Smeds at al., "Photocrosslinkable polysaccharides for in situ bydrogel formation", J. of Biomed. Mat. Res. vol. 54, No. 1, pp. 115-121 (2001).

Yoshida et al., "Convenient synthesis of polymers containing terminal aldehyde and ketone moieties by selective oxidation of polymeric terminal diols with an oxoaminium salt", Makromolecular Chemistry 194: pp. 2507-2515 (1993).

\* cited by examiner

HYALURONIC ACID BASED COPOLYMERS

CROSS-REFERENCE

This application is a divisional application of U.S. application Ser. No. 10/835,912 entitled "Hyaluronic Acid Based Copolymers" filed on Apr. 30, 2004, now U.S. Pat. No. 8,293,890, which is incorporated by reference herein in its entirety.

BACKGROUND OF THE INVENTION

1. Field of the Invention

This invention generally relates to a hyaluronic acid copolymer and compositions formed therefrom for coating an implantable medical device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient. One method of medicating a stent involves the use of a polymeric carrier coated onto the surface of the stent.

Despite their utility, stents have been plagued by two problems, namely, acute occlusion due to thrombosis and persistent occurrence of restenosis. Recent studies show that coronary stenting results in significant platelet, polymorphonuclear leukocyte, and macrophage activation, as well as activation of the coagulation pathway which induce clots despite passivation and/or anti-coagulation treatment of the stent surface. This limitation relates to the surface exposure of adhesion receptors on activated platelets to the foreign surface of the stent, producing the aforementioned thrombogenic activity that must be countered with intense anti-coagulation regimens. Subacute stent thrombosis occurs most frequently during the first few days after implantation and almost always in the first two weeks. Thereafter, neointimal cells including proliferating smooth muscle cells from the vessel wall and endothelial hyperplastic cells encompass the stent surface and ameliorate the risk of stent thrombosis.

Hyaluronic acid (HA) has been used as a material for imparting biobeneficial properties to stent coatings (see, for example, U.S. Pat. No. 5,849,368) that help reduce restenosis and thrombosis. However, HA is very hydrophilic and highly water soluble and organic solvent insoluble. Also, because of its high water solubility, HA lacks film-forming ability on an implantable device such as a stent. It is also to be note that HA molecule is delicate, that degradation of the molecule can lead to a dramatic decrease in molecular weight.

The compositions and the coatings formed thereof disclosed herein address the above described problems and other needs.

SUMMARY OF THE INVENTION

Provided herein are hyaluronic acid (HA) conjugates including HA copolymers and crosslinked HAs and compositions formed therefrom for coating implantable devices such as a stent that can be a metallic stent or a polymeric stent which can be durable, biodegradable or bioabsorbable. The HA conjugate can have molecular HA and at least a component that can be heparin, poly(ethylene glycol) (PEG), hydrophobic side chains, biocompatible hydrophobic polymers, and combinations thereof. Alternatively, the HA conjugate can have a moiety derived from HA or HA derivative and at least one moiety or derivative derived from heparin, poly (ethylene glycol) (PEG), hydrophobic side chains, biocompatible hydrophobic polymers, and combinations thereof.

The HA conjugates can be formed by functionalizing HA with a reactive agent that would provide the functionalized HA a reactive and accessible reactive group and reacting the functionalized HA with hydrophobic species, PEG, heparin, biocompatible polymers, and combinations thereof. Representative reactive agents include hydrazide, dihydrazide, aziridine, epoxides, and vinyl sulphones.

In one embodiment, crosslinked HAs can be formed by crosslinking functionalized HAs bearing crosslinking moieties in the presence of biocompatible initiator by applying a crosslinking means such as heating, UV, or combinations thereof. Crosslinking moieties such as acryloyl or methacryloyl moieties can be introduced into HA by their reaction with functionalized HA such as HA-hydrazide.

In another embodiment, crosslinked HA can be formed by reacting HA with a biocompatible crosslinker such as the aziridine crosslinker from Sybron Chemicals (New Jersey) and other crosslinkers having two or more linking moieties.

In still another embodiment, hydrophobic species, poly (ethylene glycol) (PEG), or heparin can be functionalized with two or more crosslinking moieties such as hydrazides, aziridines, epoxides, vinyl sulfphones, aldehydes and used as crosslinker to crosslink HA.

In a further embodiment, the cyclic dimmer 3-hydroxypropionatealdehyde (3-HPA) can be used as a crosslinker to crosslink HA.

The HA conjugate or crosslinked HA can be used to form a coating on an implantable device, which may include a bioactive agent. Representative bioactive agents include, but are not limited to, ABT-578™, paclitaxel, docetaxel, paclitaxel derivatives, tacrolimus, pimecrolimus, batimastat, mycophenolic acid, estradiol, clobetasol, dexamethasone, rapamycin, 40-O-(2-hydroxy)ethyl-rapamycin (everolimus), 40-O-(3-hydroxy)propyl-rapamycin, 40-O-[2-(2-hydroxy) ethoxy]ethyl-rapamycin, 40-O-tetrazole-rapamycin, 4-amino-2,2,6,6-tetramethylpiperidine-1-oxyl (4-amino-TEMPO), prodrugs thereof, co-drugs thereof, and combinations thereof.

The composition provided herein can be coated onto an implantable device. The implantable device can be any implantable device. In one embodiment, the implantable device is a drug-delivery stent. The implantable device can be used for the treatment of a medical condition such as atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

DETAILED DESCRIPTION

Provided herein are hyaluronic acid (HA) conjugates including HA copolymers and crosslinked HAs and compositions formed therefrom for coating implantable devices such as a stent that can be a metallic stent or a polymeric stent which can be durable, biodegradable or bioabsorbable. The HA conjugate can have molecular HA and at least a component that can be heparin, poly(ethylene glycol) (PEG), hydrophobic side chains, biocompatible hydrophobic polymers, and combinations thereof. Alternatively, the HA conjugate can have a moiety derived from HA or HA derivative and at least one moiety or derivative derived from heparin, poly(ethylene glycol) (PEG), hydrophobic side chains, biocompatible hydrophobic polymers, and combinations thereof. The HA containing conjugate can have organic solvent solubility and film forming property. The coating including the HA conjugate has acute and long term biobeneficial properties. In addition, the coating can provide for controlled release of a bioactive agent such as everolimus.

As used herein, biobeneficial properties of a material refers to the material capable of enhancing the biocompatibility of a device by being non-fouling, hemocompatible, actively non-thrombogenic, or anti-inflammatory, all without depending on the release of a pharmaceutically active agent. Anti-fouling is defined as preventing, delaying or reducing the amount of formation of protein build-up caused by the body's reaction to foreign material. Similarly, non-thrombogenic and anti-inflammatory means completely preventing, delaying or minimizing to a desirable degree the formation of thrombin and inflammation.

The term HA conjugate as used herein refers to a substance that includes a HA component that can be HA or a moiety derived from HA and at least one other component that can be a species or a polymer as defined herein. The components in the HA conjugate can have an interaction such as covalent bonding, ionic interaction, hydrogen bonding, van der Waals interaction, and interpenetrating network.

Modification of HA

The conjugate can be formed from a functionalized HA with a modifying species such as hydrophobic side chain species, a hydrophobic, biodegradable polymers, poly(ethylene glycol) (PEG), or heparin. The conjugate can also be formed from a HA with a functionalized modifying species.

A. Functionalization of HA

Figure 1A:
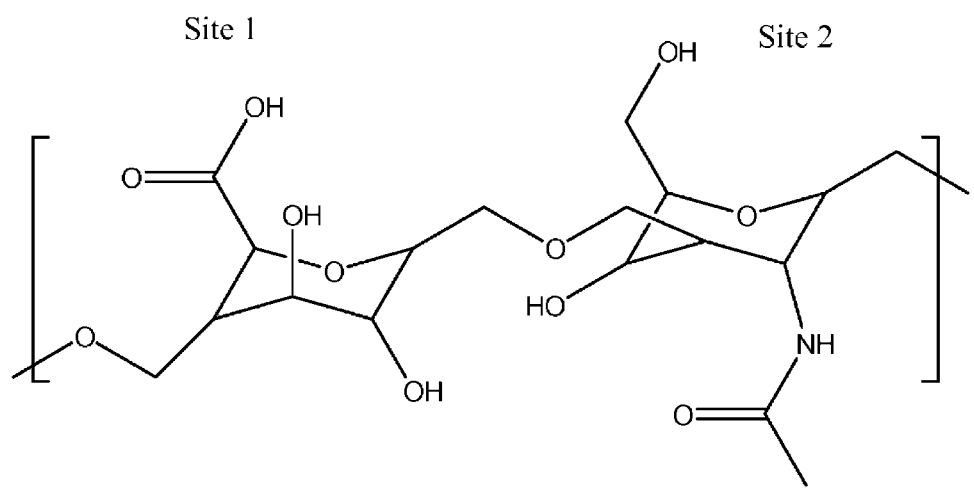
FIG. 1A is a schematic structure of hyaluronic acid's building blocks.

The HA backbone has two potential sites for functionalization, namely, a carboxylic acid and a primary hydroxyl (FIG. 1A). HA can reach molecular weights in the millions of Daltons, while its repeating unit has a molecular weight of 435 Daltons. This results in the HA molecule having a very large number of potential reactive sites, which allows one to functionalize HA via a linking agent for modification of HA.

Figure 1B:
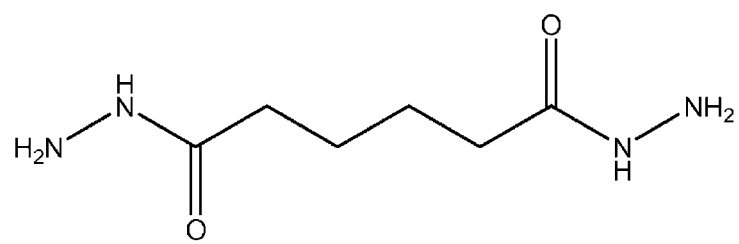
FIG. 1B shows the structure of adipic dihydrazide.

In one embodiment, the linking agent can be a difunctional reactive species having two reactive groups. One of the two reactive groups links to Site 1 or Site 2 of HA (FIG. 1A), and the other reactive group links to another polymer or material to form a modified HA such as a block copolymer comprising the HA. For example, the difunctional reactive species can be a dihydrazide. The dihydrazide can be any dihydrazide. As an example, the dihydrazide can be adipic dihydrazide (FIG. 1B). Functionalization of HA can be achieved by coupling of adipic dihydrazide with HA in the presence of an agent such as carbodiimide (ethyl carbodiimide (EDCI), for example) (see, Luo, Y., et al., J. Contr. Release 69:169-184 (2000)) (Scheme 1).

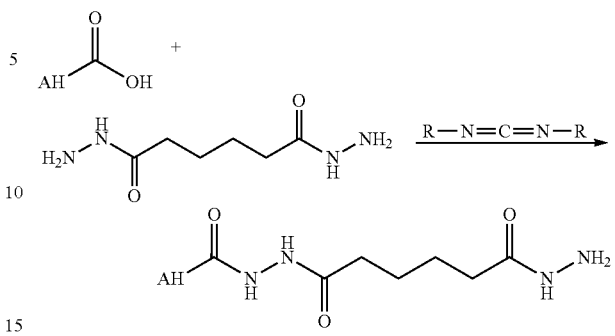

Scheme 1

The reaction can be carried out in water. In order to avoid crosslinking of HA by the dihydrazide, the reaction can be carried out in an excess of dihydrazide, and the degree of functionalization can be controlled by the amount of carbodiimide used. For example, using a stoichiometric amount of carbodiimide would result in about 100% functionalization of HA, and using 50% of the stoichiometric amount of carbodiimide would result in about 50% functionalization of HA. The amount of carbodiimide used can range from about 0% to about 100% stoichiometric amount, from about 20% to about 80% stoichiometric amount, or from about 30% to about 50% stoichiometric amount.

In another embodiment, HA can be functionalized via an aziridine, which can be conducted in water (see, for example, Gianolino, D. A., et al., Crosslinked sodium hyaluronate containing labile linkages, Abstract from Society for Biomaterials 2002). For example, HA can be functionalized by coupling with pentaerythritol tris(3-aziridinopropionate), which is commercially available, in water (scheme 2).

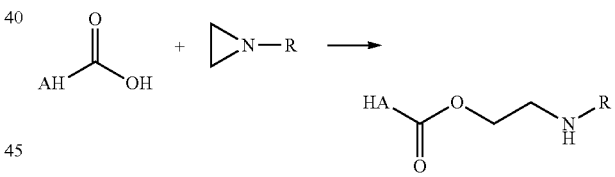

Scheme 2

In a further embodiment, the functionalization of HA can be carried out by any other suitable agents. Exemplary other suitable agents include epoxides and/or vinyl sulphones. The functionalized HA then can be coupled with another polymer or material to form a derivatized HA under conditions known in the art suitable for coupling.

The functionalized HA can bear hydrazide group, terminal amine group, terminal anhydride group, terminal aldehyde group, and combinations thereof.

B. Conjugation with Hydrophobic Species

In accordance with one embodiment of the present invention, functionalized HA can be coupled with a hydrophobic species to form a conjugate with hydrophobic side chains. Exemplary useful hydrophobic species to provide for the hydrophobic side chains of the conjugate include, for example, saturated and unsaturated fatty acids, saturated and unsaturated fatty alcohols. Exemplary useful hydrophobic, saturated and unsaturated fatty acids include, for example, castor oil, laurate, stearate, palmitate and/or oleate. Exemplary saturated and unsaturated fatty alcohols include, for example, hexanol, dodecanol, stanol, sterol, cholesterol, and/or cetyl. In some embodiments, the hydrophobic species is a short chain hydrophobic species. As used herein, the term "short chain hydrophobic species" refers to a C2-C20 hydrophobic species.

In some embodiments, a hydrophobic compound can be conjugated to HA such that the compound has a Hildebrand solubility parameter ($\delta$) less than 12 $(cal/cm^3)^{1/2}$, less than 11 $(cal/cm^3)^{1/2}$, less than 10.5 $(cal/cm^3)^{1/2}$, or alternatively less than 9 $(cal/cm^3)^{1/2}$.

In accordance with another embodiment of the present invention, the functionalized HA can be coupled with a biocompatible hydrophobic polymer, which can be non-absorbable, biodegradable or bioabsorbable. Useful biocompatible hydrophobic polymers include, for example, poly(ester amide), poly(ester amide) that may contain alkyl groups, amino acid groups, or poly(ethylene glycol) (PEG) groups, polyethylene glycol (PEG), polyhydroxyalkanoates (PHA), poly(2-hydroxyalkanoates), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalknaote) such as poly(4-hydroxybutyrate), poly(4-hydroxyvalerate), poly(4-hydroxyhexanote), poly(4-hydroxyheptanoate), poly(4-hydroxyoctanoate) and copolymers comprising any of the 3-hydroxyalkanoate or 4-hydroxyalkanoate monomers described herein or blends thereof, polyesters, poly(D,L-lactide), poly(L-lactide), polyglycolide, poly(D,L-lactide-co-glycolide), polycaprolactone, poly(D,L-lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(phosphoesters), polyphosphazenes, poly(amino acids), polysaccharides, collagen, chitosan, alginate, polyethers, polyamides, polyurethanes, polyalkylenes, polyalkylene oxides, polyethylene oxide, polypropylene oxide, polyethylene glycol (PEG), PHA-PEG, polyvinylpyrrolidone (PVP), alkylene vinyl acetate copolymers such as ethylene vinyl acetate (EVA), alkylene vinyl alcohol copolymers such as ethylene vinyl alcohol (EVOH or EVAL), poly(n-butyl methacrylate) (PBMA), SOLEF™ (poly(vinylidene fluoride-co-hexafluoropropene) and combinations thereof.

The hydrophobic side chain species and biodegradable polymers can be simply added in excess and coupled via a carbodiimide in an appropriate solvent that is a common solvent for the functionalized HA and the hydrophobic side chain species or biodegradable polymer. For example, HA-hydrizide can be coupled to high molecular weight polylactic acid with 1-ethyl-3-(3-dimethylaminopropyl)-carbodiimide (EDC) in an acetone solution with an adjusted pH for example pH=8.

While the conjugate can be formed from a functionalized HA and the hydrophobic side chain species or hydrophobic biodegradable polymers, as described above, the conjugate also can be formed from an unfunctionalized HA and a functionalized hydrophobic side chain species or hydrophobic biodegradable polymer. For example, HA can form a conjugate with commercially available octanoic hydrazide by direct coupling of the HA and octanoic hydrazide in a solvent that is a solvent for both materials.

C. Conjugation with Poly(Ethylene Glycol)

In accordance with a further aspect of the present invention, functionalized HA can form a conjugate with a high molecular weight PEG. The PEG useful for forming the HA-PEG conjugates described herein has a molecular weight in the range between 500 Daltons to 250,000 Daltons, specifically between 1,000 Daltons and 100,000 Dalton, and more specifically between 5,000 Daltons and 50,000 Daltons.

In one embodiment, PEG can be functionalized so as to form a PEG bearing a terminal aldehyde. The PEG with a terminal aldehyde can readily react at room temperature in water with a hydrazide functionalized HA to form a HA-PEG conjugate.

In another embodiment, PEG can be functionalized so as to form a PEG bearing a terminal amine group. The PEG bearing a terminal amine group can react directly with HA that was functionalized with a terminal anhydride, yielding a block copolymer, HA-co-PEG.

In a further embodiment, PEG can be functionalized so as to form a PEG succinamide. The PEG succinamide then can be coupled to HA to from a conjugate comprising HA and PEG.

PEG functionalized with amino, aldehyde, or succinyl, or combinations thereof are commercially available. For example, linear amino-PEG of average molecular weight of 6,000 Daltons can be purchased from Shearwater Polymers, Inc. (Huntsville, Ala.).

In still a further embodiment, PEG can be modified to bear an amine group, and HA can be oxidized by an oxidizing agent such as a peroxide or nitrous acid to have terminal aldehyde groups. The amine terminated PEG can then be coupled to the HA bearing terminal aldehyde groups via reductive amination to form a HA and PEG conjugate.

D. Conjugation with Heparin

In accordance with another aspect of the present invention, HA can form a conjugate with heparin. The conjugation can be achieved by coupling a functionalized HA with an unfunctionalized heparin, a functionalized heparin with an unfunctionalized HA, or a functionalized heparin with a functionalized heparin.

In one embodiment, an aldehyde terminated HA can be coupled to amino-functionalized heparin, which is commercially available, via reductive amination to form a HA/heparin conjugate.

In another embodiment, HA can be derivatized with sebacic dihydrazide as described above, PEG-dialdehyde, or a bis-succinimidyl moiety. An amine terminated heparin can then be allowed to react with the derivatized HA to form HA/heparin conjugates having sebacicdihydrazide, PEG, and bis-succinimidyl linkages, respectively.

As used herein, the term "heparin" includes molecular heparin and any of heparin derivatives. Heparin derivatives can be any functional or structural variation of heparin. Representative variations include alkali metal or alkaline-earth metal salts of heparin, such as sodium heparin (e.g., hepsal or pularin), potassium heparin (e.g., clarin), lithium heparin, calcium heparin (e.g., calciparine), magnesium heparin (e.g., cutheparine), and low molecular weight heparin (e.g., ardeparin sodium). Other examples include heparin sulfate, heparinoids, heparin based compounds and heparin having a hydrophobic counter-ion.

The HA conjugates described herein can take a variety of formulae. In one embodiment, the conjugate can be HA-co-PEG or HA-co-heparin, which is end-capped with hydrophobic species such as fatty acids such as stearate, laurate, palmitate, and oleate, fatty alcohols such as hexanol, dodecanol, stanol, sterol, cholesterol, and cetyl, or biodegradable hydrophobic polymers such as poly(ester amide) that may optionally contain alkyl, amino acid, PEG or alcohol groups, polycaprolactone, polylactide, polyglycolide, polyhydroxyalkanoate (PHA), polydioxanone (PDS), or PHA-PEG. The PHA may include poly($\alpha$-hydroxyacids), poly(β-hydroxyacid) such as poly(3-hydroxybutyrate) (PHB), poly(3-hydroxybutyrate-co-valerate) (PHBV), poly (3-hydroxyproprionate) (PHP), poly(3-hydroxyhexanoate) (PHH), or poly(4-hydroxyacid) such as poly(4-hydroxybutyrate), poly(4-hydroxyvalerate) or poly(4-hydroxyhexanoate). The hydrophobic species or biodegradable hydrophobic polymers can be side chains attached to HA-co-PEG or HA-co-heparin.

In one embodiment, the HA conjugate is a PEG-HA-(C12-C18 alkyl) conjugate.

E. Crosslinking of Functionalized HA

In accordance with a further embodiment of the present invention, a modified HA can be crosslinked using a crosslinker. Because of the high hydrophilicity of HA, modified HAs may become a weak hydrogel when immersed in water. Crosslinking of the modified HA would lead to the formation of a coating comprising the modified HA.

In one embodiment, acrylic moieties can be introduced into a modified HA by reacting a HA-hydrazide with acryloyl or methacryloyl chloride to form a HA bearing olefinic moieties such as acryloyl or methacryloyl groups. This material can be mixed with a biocompatible initiator, applied to an implantable device by, for example, dip coating, and then crosslinked upon exposure to a radiation, for example, UV radiation.

In another embodiment, an un-functionalized HA and a crosslinking agent with multiple aziridine groups can be separately applied to the surface of an implantable device to coat and left to react at a temperature such as an ambient temperature. The crosslinking agent can be, for example, pentaerythritol tris(3-aziridinopropionate) available from Sybron Chemicals (NJ). Any other agents having multiple aziridine groups can also be employed.

In a further embodiment of the present invention, a hydrophobic side chain species described herein or a polymer such as PEG can be functionalized with two or more hydrazides, aziridines, aldehydes, amines, diacrylate, bisacrylamide, and other functionalities for use as crosslinkers. A functionalized or un-functionalized HA can be subjected to crosslink with these crosslinkers with or without heating. An example of a hydrophobic side chain species is cyclic dimmer 3-hydroxypropionatealdehyde (3-HPA) found in reuterin.

In still a further embodiment, HA can be coupled to a polymeric surface on an implantable device via, for example, plasma treatment. The surface can be first treated with an argon (Ar) and $NH_3$ plasma to attach amine functionalities that can then be reacted with an anhydride, for example, succinic anhydride, to the surface. These functionalities can then be coupled to one or more functionalized HA, e.g., HA-hydrazide in the presence of a carbodiimide to form a crosslinked HA surface. If desirable, the crosslinked HA surface can be further modified with a biobeneficial material such as heparin. The biobeneficial material can be functionalized with one or more crosslinking moieties such as hydrazide or aziridine groups, with or without a PEG spacer, and attached to the crosslinked HA surface after dip coating.

Bioactive Agent

The modified HA described herein can be used to form coating compositions that may include one or more bioactive agents. The bioactive agent can be any agent which is biologically active, for example, a therapeutic, prophylactic, or diagnostic agent. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight, for example, between about 100 and about 500,000 grams or more per mole or between about 100 and about 500,000 grams or more per mole, can be encapsulated. Some other examples of suitable materials include proteins such as antibodies, receptor ligands, and enzymes, peptides such as adhesion peptides, and saccharides and polysaccharides. Some further examples of materials which can be included include blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. Representative diagnostic agents are agents detectable by x-ray, fluorescence, magnetic resonance imaging, radioactivity, ultrasound, computer tomography (CT) and positron emission tomagraphy (PET).

In the case of controlled release, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect for the patient. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimics, 4-amino-2,2,6,6-tetramethylpiperidine-1-oxyl (4-amino-TEMPO), sirolimus and sirolimus derivatives, paclitaxel and paclitaxel derivatives, estradiol, steroidal anti-inflammatory agents, antibiotics, anticancer agents, dietary supplements such as various vitamins, and a combination thereof. An example of an antiallergic agent is permirolast potassium. Other therapeutic substances or agents which may be appropriate include alpha-interferon, genetically engineered epithelial cells, ABT-578™, paclitaxel, docetaxel, paclitaxel derivatives, tacrolimus, pimecrolimus, batimastat, mycophenolic acid, estradiol, clobetasol, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl (4-amino-TEMPO), prodrugs thereof, co-drugs thereof, and combinations thereof.

The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Coatings on Implantable Devices

Compositions having any of the HA conjugates and/or crosslinked HAs can be used to coat implantable devices, with or without a bioactive agent. The coating described herein can be formed as a single layer of coating on an implantable device or in conjunction with, such as on top of, another layer of coating including a polymer other than the HA conjugate or crosslinked HA described herein. In some embodiments, the HA coating could be the outmost layer of a coated device. In other embodiments, the HA layer could be a top coat layer for a polymer-drug reservoir layer or a polymer free drug layer.

The HA conjugate or crosslinked HA can also be blended with one or more polymers such as biocompatible and/or bioabsorbable polymers. Examples include, but not limited to, poly(ester amide), poly(ester amide) that may optionally contain alkyl groups, amino acid groups, or poly(ethylene glycol) (PEG) groups, polyethylene glycol (PEG), polyhydroxyalkanoates (PHA), poly(2-hydroxyalkanoates), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalknaote) such as poly(4-hydroxybutyrate), poly(4-hydroxyvalerate), poly(4-hydroxyhexanote), poly(4-hydroxyheptanoate), poly(4-hydroxyoctanoate) and copolymers comprising any of the 3-hydroxyalkanoate or 4-hydroxyalkanoate monomers described herein or blends thereof, polyesters, poly(D,L-lactide), poly(L-lactide), polyglycolide, poly(D,L-lactide-co-glycolide), polycaprolactone, poly(D,L-lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(phosphoesters), polyphosphazenes, poly(amino acids), polysaccharides, collagen, chitosan, alginate, polyethers, polyamides, polyurethanes, polyalkylenes, polyalkylene oxides, polyethylene oxide, polypropylene oxide, polyethylene glycol (PEG), PHA-PEG, polyvinylpyrrolidone (PVP), alkylene vinyl acetate copolymers such as ethylene vinyl acetate (EVA), alkylene vinyl alcohol copolymers such as ethylene vinyl alcohol (EVOH or EVAL), poly(n-butyl methacrylate) (PBMA) and combinations thereof. In one preferred embodiment, the blend is with SOLEF™ (poly(vinylidene fluoride-co-hexafluoropropene).

In another embodiment, the composition described herein can be used for coating an implantable device such as a drug-delivery stent for controlled release of a bioactive agent. The composition may comprise any of HA conjugates or crosslinked HAs alone or as a blend component with other biocompatible polymers.

In some further embodiments, with the chemistries mentioned previously different type of networks and architectures can be achieved. Exemplary such architectures can be, for example, physical crosslinking or interpenetrating networks. In one embodiment, an interpenetrating network (IPN) can be made by locking HA in a tightly crosslinked network of PEG diacrylate. In this IPN, the HA is not covalently bound to the crosslinked polymer, but trapped in the network. HA can also be physically locked in the coating by being applied simultaneously with an ultra high molecular weight polymer such as poly(D,L-lactide). In addition, HA can be covalently bound to a thermoreversible gel based on a N-isopropylacrylamide (NIPAM)-PEG diblock copolymer.

Method of Coating a Device

The composition described herein can be coated on an implantable device such as a stent by spray coating or any other coating process available in the art. Generally, the coating involves dissolving or suspending the composition, or one or more components thereof, in a solvent or solvent mixture to form a solution, suspension, or dispersion of the composition or one or more components thereof, applying the solution or suspension to an implantable device, and removing the solvent or solvent mixture to form a coating or a layer of coating. Suspensions or dispersions of the composition described herein can be in the form of latex or emulsion of microparticles having a size between 1 nanometer and 100 microns, preferably between 1 nanometer and 10 microns. Heat and/or pressure treatment can be applied to any of the steps involved herein. In addition, if desirable, the coating described here can be subjected to further heat and/or pressure treatment. Some additional exemplary processes of coating an implantable device that may be used to form a coating on an implantable using the composition described herein are described in, for example, Lambert T L, et al. Circulation, 1994; 90: 1003-1011; Hwang C W, et al. Circulation, 2001; 104: 600-605; Van der Giessen W J, et al. Circulation, 1996; 94: 1690-1697; Lincoff A M, et al. J Am Coll Cardiol 1997; 29: 808-816; Grube E. et al, J American College Cardiology Meeting, Mar. 6, 2002, ACCIS2002, poster 1174-15; Grube E, et al, Circulation, 2003, 107: 1, 38-42; Bullesfeld L, et al. Z Kardiol, 2003, 92: 10, 825-832; and Tanabe K, et al. Circulation 2003, 107: 4, 559-64.

The composition can be coated onto the implantable device in the form of a single layer of coating or components of the composition can be coated onto the device in the form of separate layers of coating.

The bioactive agent can be coated onto an implantable device as a separate layer or together with the composition having any of the HA conjugates or crosslinked HAs. In one embodiment, the bioactive agent is coated onto the device as a separate layer. In another embodiment, the bioactive agent is coated onto the device together with the composition described herein.

In a further embodiment, the bioactive agent or a second bioactive agent can be loaded onto a coating described here by swell-loading. The composition having one or more of HA conjugates and/or functionalized HAs can be formulated with a crosslinker such as hydrazides, aziridines, aldehydes, amines, diacrylate, bisacrylamide and applied on top of a medical device coating. Upon photoactivated or thermally initiated crosslinking, a thin surface gel comprising the one or more of the HA conjugates or crosslinked HAs described herein would form. The bioactive agent described herein and/or a second drug can then be swell-loaded in this surface gel. The swell loaded bioactive agent can have a fast release rate, e.g., about 50% to 100% release in vivo in a period of, for example, from about one, two, or three hours to about one day or two days. This would allow the forming of a medical device coating system that has a bimodal release rate that may be efficacious for more refractory lesions such as diabetes, long vessel, high cholesterol, or vulnerable plaques by forming a coating with a first agent that has a controlled release of the first agent and a surface gel described herein with a second agent swell loaded therein. The first agent and the second agent can be the same agent or different agents, which are described above.

As used herein, the term "solvent" refers to a liquid substance or composition that is compatible with the polymer and/or the drug is capable of dissolving or suspending the drug and/or polymeric composition or one or more components thereof at a desired concentration. Representative examples of solvents include chloroform, acetone, water (buffered saline), dimethylsulfoxide (DMSO), propylene glycol monomethyl ether (PM,) iso-propylalcohol (IPA), n-propyl alcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, 1,1,2-trichloroethane, formamide, hexafluoroisopropanol, 1,1,1-trifluoroethanol, and hexamethyl phosphoramide and a combination thereof.

Examples of medical devices that can be used with the chemicals of the present invention include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In one embodiment, the implantable device is a metallic stent or a biodegradable or bioabsorbable stent.

The compositions described herein can be coated onto a bare metallic or polymeric implantable device or on top of a drug eluting or drug delivery systems.

Method of Use

In accordance with embodiments of the invention, a coating of the various described embodiments can be formed on an implantable device or prosthesis, e.g., a stent. For coatings including one or more active agents, the agent will be retained on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device comprising a coating described herein can be used to treat an animal having a condition or disorder that requires a treatment. Such an animal can be treated by, for example, implanting a device described herein in the animal. Preferably, the animal is a human being. Exemplary disorders or conditions that can be treated by the method disclosed herein include, but not limited to, atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

EXAMPLES

The embodiments of the present invention will be illustrated by the following set forth examples. All parameters and data are not to be construed to unduly limit the scope of the embodiments of the invention.

Example 1

A stent can be coated according to the procedure and in the configuration as specified below:
Primer layer: 100 μg of PLA;
Matrix drug layer: 500 μg of poly(lactic acid) (PLA) and everolimus (weight ratio of PLA to everolimus can be 1:1, for example); and
Topcoat layer: 300 μg of HA conjugate blended with PLA (weight ratio of HA conjugate to everolimus can be 1:1, for example).

Example 2

A stent can be coated according to the procedure and in the configuration as specified below:
Primer layer: 100 μg of PLA;
Matrix drug layer: 500 μg of PLA and everolimus (weight ratio of PLA to everolimus can be 1:1, for example); and
Topcoat layer: 300 μg HA conjugate blended with PEGlyated PLA (e.g. triblock PLA-PEG-PLA) (weight ratio of HA conjugate to PEGlyated PLA can be 1:1, for example)

Example 3

A stent can be coated according to the procedure and in the configuration as specified below:
Primer layer: 100 μg of PLA;
Matrix drug layer: 500 μg of PLA and everolimus (weight ratio of PLA to everolimus can be 1:1, for example); and
Topcoat layer: 300 μg pure HA conjugate.
While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

Additional Embodiments

1. A hyaluronic acid (HA) conjugate comprising HA and at least a component selected from the group consisting of
heparin,
poly(ethylene glycol) (PEG),
hydrophobic side chains,
biocompatible hydrophobic polymers, and
combinations thereof.

2. The HA conjugate of embodiment 1 wherein the short hydrophobic side chains are selected from the group consisting of saturated and unsaturated fatty acids and fatty alcohols.

3. The HA conjugate of embodiment 1 wherein the biocompatible hydrophobic polymers are selected from the group consisting of poly(ester amide), poly(ester amide) that may contain alkyl groups, amino acid groups, or poly(ethylene glycol) (PEG) groups, polyethylene glycol (PEG), polyhydroxyalkanoates (PHA), polyesters, poly(D,L-lactide), poly(L-lactide), polyglycolide, poly(D,L-lactide-co-glycolide), polycaprolactone, poly(D,L-lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(phosphoesters), polyphosphazenes, poly(amino acids), polysaccharides, collagen, chitosan, alginate, polyethers, polyamides, polyurethanes, polyalkylenes, polyalkylene oxides, polyethylene oxide, polypropylene oxide, polyethylene glycol (PEG), PHA-PEG, polyvinylpyrrolidone (PVP), alkylene vinyl acetate copolymers such as ethylene vinyl acetate (EVA), alkylene vinyl alcohol copolymers such as ethylene vinyl alcohol (EVOH or EVAL), poly(n-butyl methacrylate) (PBMA), SOLEF™ (poly(vinylidene fluoride-co-hexafluoropropene) and combinations thereof.

4. The HA conjugate of embodiment 3 wherein the PHA is selected from the group consisting of poly(2-hydroxyalkanoates), poly(3-hydroxyalkanoates), poly(3-hydroxypropanoate), poly(3-hydroxybutyrate), poly(3-hydroxyvalerate), poly(3-hydroxyhexanoate), poly(3-hydroxyheptanoate), poly(3-hydroxyoctanoate), poly(4-hydroxyalkanoate), poly(4-hydroxybutyrate), poly(4-hydroxyvalerate), poly(4-hydroxyhexanote), poly(4-hydroxyheptanoate), poly(4-hydroxyoctanoate) and copolymers comprising any of the 3-hydroxyalkanoate or 4-hydroxyalkanoate monomers described herein or blends thereof, and combinations thereof.

5. The HA conjugate of embodiment 1 wherein the hydrophobic side chains are selected from the group consisting of castor oil, laurate, state, palmitate, oleate, hexanol, dodecanol, stanol, sterol, cholesterol, cetyl, and combination thereof.

6. The HA conjugate of embodiment 1 comprising a heparin and a crosslinker which comprises a moiety selected from the group consisting of difunctional carbodiimide, PEG-dialdehyde, and a bis-succinidyl moieties.

7. The HA conjugate of embodiment 1 comprising a poly (ester amide) which optionally comprises one or more groups selected from the group consisting of alkyl, amino acids, PEG, and combinations thereof.

8. The HA conjugate of embodiment 1 wherein the biocompatible polymer is biodegradable.

9. The HA conjugate of embodiment 1 which is a copolymer comprising a PEG-HA-(C12-C18 alkyl) conjugate.

10 A crosslinked HA composition produced by a process comprising
crosslinking a HA having crosslinking groups by a crosslinking means selected from the group consisting of photo radiation, heating, chemical reaction, physical crosslinking, and combinations thereof.

11. The crosslinked HA composition of embodiment 10 wherein the crosslinking groups are olefinic groups, and
wherein the crosslinking means is photo radiation.

12. The crosslinked HA composition of embodiment 11 wherein the olefinic groups are selected from the group consisting of acryloyl groups, methacryloyl groups, and combinations thereof.

13. A crosslinked HA composition produced by a process comprising
crosslinking HA with a crosslinker by chemical reaction.
14. The crosslinked HA composition of embodiment 13 wherein the crosslinker comprises a hydrophobic moiety or PEG and two or more crosslinking moieties.
15. The crosslinked HA composition of embodiment 14 wherein the hydrophobic moiety is selected from the group consisting of saturated and unsaturated fatty acids, fatty alcohols, hydrophobic polymers, and combinations thereof; and
wherein the two or more crosslinking moieties are selected from the group consisting of hydazides, azeridines, aldehydes, amines, diacrylate, bisacrylamide, and combinations thereof.
16. The crosslinked HA composition of embodiment 14 wherein the hydrophobic moiety is selected from the group consisting of castor oil, laurate, state, palmitate, oleate, hexanol, dodecanol, stanol, sterol, cholesterol, cetyl, poly(ester amides), poly(caprolactone), polylactide, polyglycolide, poly(lactide-co-glycolide), poly(DL-lactide-co-glycolide), polyhydroxyalkanoate (PHA), poly(3-hydroxybutyrate) (PHB), poly(3-hydroxybutyrate-co-valerate) (PHBV), poly (3-hydroxyproprionate) (PHP), poly(3-hydroxyhexanoate) (PHH), poly(4-hydroxybutyrate), poly(4-hydroxyvalerate); poly(4-hydroxyhexanoate), poly(dioxanone), and PHA-PEG, and a combination thereof.
17. The crosslinked HA composition of embodiment 15 wherein the crosslinker is cyclic dimmer of 3-hydroxypropionatealdehyde.
18. An implantable device comprising the HA conjugate of embodiment 1.
19. An implantable device comprising the HA conjugate of embodiment 2.
20. An implantable device comprising the HA conjugate of embodiment 3.
21. An implantable device comprising the HA conjugate of embodiment 4.
22. An implantable device comprising the HA conjugate of embodiment 5.
23. An implantable device comprising the HA conjugate of embodiment 6.
24. An implantable device comprising the HA conjugate of embodiment 7.
25. An implantable device comprising the HA conjugate of embodiment 8.
26. An implantable device comprising the HA conjugate of embodiment 9.
27. An implantable device comprising the crosslinked HA composition of embodiment 10.
28. An implantable device comprising the crosslinked HA composition of embodiment 11.
29. An implantable device comprising the crosslinked HA composition of embodiment 12.
30. An implantable device comprising the crosslinked HA composition of embodiment 13.
31. An implantable device comprising the crosslinked HA composition of embodiment 14.
32. An implantable device comprising the crosslinked HA composition of embodiment 15.
33. An implantable device comprising the crosslinked HA composition of embodiment 16.
34. An implantable device comprising the crosslinked HA composition of embodiment 17.
35. The implantable device of embodiment 18 further comprising a bioactive agent.
36. The implantable device of embodiment 18 further comprising a bioactive agent selected from the group consisting of ABT-578™, paclitaxel, docetaxel, paclitaxel derivatives, tacrolimus, pimecrolimus, batimastat, mycophenolic acid, estradiol, clobetasol, dexamethasone, rapamycin, 40-O-(2-hydroxy)ethyl-rapamycin (everolimus), 40-O-(3-hydroxy) propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl (4-amino-TEMPO), prodrugs thereof, co-drugs thereof, and combinations thereof.
37. The implantable device of embodiment 27 further comprising a bioactive agent.
38. The implantable device of embodiment 27 further comprising a bioactive agent selected from the group consisting of ABT-578™, paclitaxel, docetaxel, paclitaxel derivatives, tacrolimus, pimecrolimus, batimastat, mycophenolic acid, estradiol, clobetasol, dexamethasone, rapamycin, 40-O-(2-hydroxy)ethyl-rapamycin (everolimus), 40-O-(3-hydroxy) propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl (4-amino-TEMPO), prodrugs thereof, co-drugs thereof, and combinations thereof.
49. A method of treating a disorder selected from the group consisting of atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof, comprising:
implanting in the human being the implantable device of embodiment 18.
50. A method of treating a disorder selected from the group consisting of atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof, comprising:
implanting in the human being the implantable device of embodiment 27.
51. A hyaluronic acid (HA) conjugate comprising a moiety derived from HA and at least one moiety derived from a material selected from the group consisting of
heparin,
poly(ethylene glycol) (PEG),
hydrophobic side chains,
biocompatible hydrophobic polymers, and
combinations thereof.
52. An implantable device comprising the HA conjugate of embodiment 51.
53. The implantable device of embodiment 52 further comprising a bioactive agent.
54. A method of treating a disorder selected from the group consisting of atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof, comprising:
implanting in the human being the implantable device of embodiment 53.

What is claimed is:
1. A hyaluronic acid (HA) conjugate comprising the reaction product of a moiety derived from HA and a moiety derived from poly(ethylene glycol) (PEG); wherein the moiety derived from HA is a HA functionalized to bear a terminal amine group, a terminal anhydride group, or a terminal aldehyde group, wherein the moiety derived from PEG is a PEG functionalized to bear a terminal aldehyde group, a succina- mide group, or a terminal amine group; wherein the resulting HA conjugate with PEG is end-capped with a species selected from the group consisting of fatty acid, fatty alcohol, poly (ester amide) that may optionally contain alkyl, amino acid, PEG or alcohol group, polycaprolactone, polylactide, polyglycolide, polyhydroxyalkanoate (PHA), polydioxanone (PDS), or PHA-PEG.

2. An implantable device comprising the HA conjugate of claim 1.

3. The implantable device of claim 2, further comprising a bioactive agent.

4. The implantable device of claim 3, wherein the bioactive agent is selected from the group consisting of ABT-578™, paclitaxel, docetaxel, paclitaxel derivatives, tacrolimus, pimecrolimus, batimastat, mycophenolic acid, estradiol, clobetasol, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 4-amino-2,2,6,6-tetramethylpiperidine-1-oxyl (4-amino-TEMPO), prodrugs thereof, co-drugs thereof, and combinations thereof.

5. A method of treating a disorder selected from the group consisting of atherosclerosis, thrombosis, restenosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof, comprising: implanting in a human being an implantable device comprising the HA conjugate of claim 1 and optionally a bioactive agent.

6. The implantable device of claim 2, which is a stent.

7. The HA conjugate of claim 1, wherein the fatty acid is selected from the group consisting of stearate, laurate, palmitate, and oleate.

8. The HA conjugate of claim 1, wherein the fatty alcohol is selected from the group consisting of hexanol, dodecanol, stanol, sterol, cholesterol, and cetyl alcohol.

9. The HA conjugate of claim 1, wherein the PHA is selected from the group consisting of poly($\alpha$-hydroxyacids), poly($\beta$-hydroxyacid), poly(3-hydroxybutyrate) (PHB), poly(3-hydroxybutyrate-co-valerate) (PHBV), poly(3-hydroxypropionate) (PHP, poly(3-hydroxyhexanoate) (PHH), poly(4-hydroxyacid), poly(4-hydroxybutyrate), poly(4-hydroxyvalerate), and poly(4-hydroxyhexanoate).

10. The HA conjugate of claim 1, The HA conjugate of claim 1, wherein the HA conjugate is a PEG-HA-(C12-C18 alkyl) conjugate.

* * * * *